(12) United States Patent
Imbalzano et al.

(10) Patent No.: US 7,147,912 B2
(45) Date of Patent: *Dec. 12, 2006

(54) AMPHIPATHIC PROTEINACEOUS COATING ON NANOPOROUS POLYMER

(75) Inventors: John Francis Imbalzano, Elkton, MD (US); Barry Stieglitz, Wynnewood, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 73 days.

This patent is subject to a terminal disclaimer.

(21) Appl. No.: 10/920,580

(22) Filed: Aug. 18, 2004

(65) Prior Publication Data

US 2006/0040098 A1   Feb. 23, 2006

(51) Int. Cl.
B32B 3/26 (2006.01)
B32B 9/00 (2006.01)
C07K 1/00 (2006.01)

(52) U.S. Cl. .............................. 428/304.4; 428/318.4; 530/350

(58) Field of Classification Search ............ 428/304.4, 428/318.4; 530/350
See application file for complete search history.

(56) References Cited

U.S. PATENT DOCUMENTS

| | | |
|---|---|---|
| 4,754,009 A | 6/1988 | Squire |
| 4,897,457 A | 1/1990 | Nakamura et al. |
| 4,935,477 A | 6/1990 | Squire |
| 5,543,217 A | 8/1996 | Morgan |
| 5,663,255 A | 9/1997 | Anolick et al. |
| 5,883,177 A | 3/1999 | Colaianna et al. |
| 5,919,878 A | 7/1999 | Brothers et al. |
| 6,015,609 A * | 1/2000 | Chaouk et al. .......... 428/308.4 |
| 2003/0113454 A1 | 6/2003 | De Vocht et al. |
| 2003/0134042 A1 | 7/2003 | De Vocht et al. |
| 2003/0166960 A1 | 9/2003 | De Vocht et al. |

FOREIGN PATENT DOCUMENTS

| | | |
|---|---|---|
| WO | WO 00/37971 | 6/2000 |
| WO | WO 00/58342 | 10/2000 |
| WO | WO 01/57528 A1 | 8/2001 |
| WO | WO 02/10221 A1 | 2/2002 |
| WO | WO 2004/000880 A1 | 12/2003 |
| WO | WO 2005/068087 A2 | 7/2005 |

OTHER PUBLICATIONS

Janssen et al., Biomaterials 23 (2002) 4847-4854.*
Paul Holister et al, Nanoporous Materials, Technology White Papers, NR. 5, Oct. 2003, Cientifica, LTD.
A. Yu. Alentieve et al, High Transport Parameters and Free vol. of Perfluorodioxole Copolymers, Journal of Membrane Science, vol. 126, No. 1, Apr. 2, 1997.
Ming-H. Hung, Structure-Property Relationship of Fluorinated Dioxole Polymers, Macromolecules 1993, 26, 5829-5834, 1993 American Chemical Society, Abstract Published in Advance ACS Abstracts, Oct. 1, 1993.
V. Teplyakov et al, Correlation Aspects of the Selective Gas Permeabilities of Polymeric Materials and Membranes, Gas Separation & Purification, vol. 4, Jun. 1990, pp. 66-74.
Y. Kobayashi et al, Free vol. and Physical Again of Poly(Vinyl Acetate) Studied by Positron Annihilation, Macromolecules 1989, 22, pp. 2302-2306, 1989 American Chemical Society.
J. Liu, Free-vol. Distributions of Polystyrene Probed by Positron Annihilation: Comparison with Free-vol. Theories, Macromolecules 1993, 26, pp. 7149-7155, 1993 American Chemical Society.
H. A. B. Wosten et al, Interfacial Self-Assembly of a Schizophyllum Commune Hydrophobin into an Insoluble Amphipathic Protein Membrane Depends on Surface Hydrophobicity, Colloids and Surfaces B: Biointerfaces, 5, 1995, pp. 189-195.
Scholtmeijer et al, Surface Modifications Created by using Engineered Hydrophobins, Applied and Environmetnal Microbiology, Mar. 2002, pp. 1367-1373, 2002 American Society for Microbiology.
N. Mozes et al, Microbial Cell Surface Analysis, Structural and Physicochemical Methods, 1991, pp. 261-267.
M. J. Bailey et al, Process Technological Effects of Deletion and Amplification of Hydrophobins I and II in Transformants of Trichoderma Reesei, Appl Microbiol Biotechnol (2002) 58: 721-727. Mar. 7, 2002.
M. Linder et al, The Hydrophobins HFBI and HFBII From Trichoderma Reesei Showing Efficient Internations with Nonionic Surfactants in Aqueous Two-Phase Systems, Biomacromolecules 2001, 2, 511-517.
H. A. B. Wosten, Interfacial Self-Assembly of a Fungal Hydrophobin into a Hydrophobic Rodlet Layer, the Plant Cell, vol. 5, 1567-1574, Nov. 1993, 1993 American Society of Plant Physiologists.
Joseph G. H. Wessels, "Hydrophobins: Proteins that Change the Nature of the Fungal Surface", Advances in Microbial Physiology, Academic Press, London, GB, vol. 38, No. 38, 1997, pp. 1-45.
Scholmeijer K et al: "Fungal Hydrophobins in Medical and Technical Applications", Applied Microbiology and Biotechnology, Springer Verlag, Berlin, Germany, vol. 56, No. 1/2, Jul. 2001, pp. 1-8.

* cited by examiner

Primary Examiner—Terrel Morris
Assistant Examiner—Victor S. Chang

(57) ABSTRACT

The present invention relates to the formation of amphipathic proteinaceous coatings on nanoporous polymers.

6 Claims, No Drawings

SEQUENCE LISTING

<160> NUMBER OF SEQ ID NOS: 4

<210> SEQ ID NO 1
<211> LENGTH: 135
<212> TYPE: PRT
<213> ORGANISM: Talaromyces thermophilus

<400> SEQUENCE: 1

```
Leu Pro Asn Val Gly Pro Ser Gly Lys Thr Ala His Lys Pro His Gln
1               5                   10                  15

Glu Pro Phe Trp Pro Val Gln Gln Asp Val Thr Val Glu Gln Ala Lys
            20                  25                  30

Ala Ile Cys Gly Glu Gly Asn Gln Val Ala Cys Cys Asn Glu Val Ser
        35                  40                  45

Tyr Ala Gly Asp Thr Thr Glu Ile Ala Thr Gly Pro Leu Ala Gly Thr
    50                  55                  60

Leu Lys Asp Leu Leu Gly Gly Lys Asn Gly Ala Lys Gly Leu Gly Leu
65                  70                  75                  80

Phe Asp Lys Cys Ser Arg Leu Asn Val Asp Leu Leu Gly Leu Ser
                85                  90                  95

Ser Leu Ile Asn Gln Glu Cys Lys Gln His Ile Ala Cys Cys Gln Gly
            100                 105                 110

Asn Glu Ala Asp Ser Ser Asn Asp Leu Ile Gly Leu Asn Ile Pro Cys
        115                 120                 125

Ile Ala Leu Gly Ser Leu Leu
        130             135
```

<210> SEQ ID NO 2
<211> LENGTH: 405
<212> TYPE: DNA
<213> ORGANISM: Talaromyces thermophilus

<400> SEQUENCE: 2

```
ctgccaaacg tcggtcccag tgggaagacg gctcacaagc cgcaccagga gcctttctgg     60
cctgtgcagc aggacgtgac cgtggaacag gccaaggcta tctgtggtga aggcaaccag    120
gtcgcttgct gcaacgaggt cagctacgcg ggcgacacca ccgaaatcgc gaccggcccc    180
ctggctggca ccctcaagga cctgctcggc ggcaagaacg gcgccaaggg cctgggtctc    240
ttcgacaagt gctcgcgtct caatgtcgat ctcctgcttg gcctgtcgag cctcatcaac    300
caagaatgca agcagcacat tgcctgctgc cagggcaacg aggccgattc ctccaacgac    360
ctcatcggtc tcaacattcc ttgcattgcc cttggctcgc tgctg                    405
```

<210> SEQ ID NO 3
<211> LENGTH: 151
<212> TYPE: PRT
<213> ORGANISM: Talaromyces thermpohilus

<400> SEQUENCE: 3

```
Met Lys Phe Ala Gly Val Leu Leu Ala Val Ala Ala Ala Thr Ala
1               5                   10                  15

Leu Pro Asn Val Gly Pro Ser Gly Lys Thr Ala His Lys Pro His Gln
            20                  25                  30

Glu Pro Phe Trp Pro Val Gln Gln Asp Val Thr Val Glu Gln Ala Lys
            35                  40                  45

Ala Ile Cys Gly Glu Gly Asn Gln Val Ala Cys Cys Asn Glu Val Ser
```

-continued

```
                    50                  55                  60
Tyr Ala Gly Asp Thr Thr Glu Ile Ala Thr Gly Pro Leu Ala Gly Thr
65                  70                  75                  80

Leu Lys Asp Leu Leu Gly Gly Lys Asn Gly Ala Lys Gly Leu Gly Leu
                85                  90                  95

Phe Asp Lys Cys Ser Arg Leu Asn Val Asp Leu Leu Leu Gly Leu Ser
            100                 105                 110

Ser Leu Ile Asn Gln Glu Cys Lys Gln His Ile Ala Cys Cys Gln Gly
        115                 120                 125

Asn Glu Ala Asp Ser Ser Asn Asp Leu Ile Gly Leu Asn Ile Pro Cys
    130                 135                 140

Ile Ala Leu Gly Ser Leu Leu
145                 150

<210> SEQ ID NO 4
<211> LENGTH: 453
<212> TYPE: DNA
<213> ORGANISM: Talaromyces thermophilus

<400> SEQUENCE: 4
atgaagttcg ccggtgtctt gcttgctgtc gccgctgcgg cgactgccct gccaaacgtc      60
ggtcccagtg ggaagacggc tcacaagccg caccaggagc ctttctggcc tgtgcagcag     120
gacgtgaccg tggaacaggc caaggctatc tgtggtgaag caaccaggt cgcttgctgc      180 aacgaggtca gctacgcggg cgacaccacc gaaatcgcga ccggccccct ggctggcacc     240
ctcaaggacc tgctcggcgg caagaacggc gccaagggcc tgggtctctt cgacaagtgc     300
tcgcgtctca atgtcgatct cctgcttggc ctgtcgagcc tcatcaacca agaatgcaag     360
cagcacattg cctgctgcca gggcaacgag gccgattcct ccaacgacct catcggtctc     420
aacattcctt gcattgccct tggctcgctg ctg                                   453
```

AMPHIPATHIC PROTEINACEOUS COATING ON NANOPOROUS POLYMER

FIELD OF THE INVENTION

This invention relates to modification of the water-wettability on the surface of nanoporous polymer.

DESCRIPTION OF RELATED ART

WO 2004/000880 A1 discloses the coating of surfaces with a proteinaceous material called hydrophobin to form an amphipathic coating on such surfaces. Amphipathic means that the proteinaceous material provides both hydrophobic and hydrophilic groups to the coating (see definition of amphipathic in IUPAC Compendium of Chemical technology, $2^{nd}$ Ed, 31, 612 (1972)). Hydrophobins are examples of one class of such proteinaceous material. According to the amphipathic nature of the hydrophobin the proteinaceous material self-assembles at the surface of a substrate being coated to form a coating, such coating possessing both hydrophobicity and hydrophilicity oriented in accordance with the wettability of the surface being coated. If the surface is hydrophobic, the hydrophobic side of the coating is in contact with the hydrophobic surface being coated, and the outer surface of the coating is hydrophilic, thereby increasing the water wettability of the surface being coated. Hydrophobin-like materials are disclosed in WO 2004/000880 as being not only hydrophobins isolated from nature, but also chemically modified or genetically modified hydrophobins, but still having the hydrophobin property of self-assembly at hydrophilic or hydrophobic interfaces into amphipathic membranes (coatings). For simplicity, the term "hydrophobin" as used herein will include the hydrophobin-like materials. The hydrophobin prior to self-assembly is sometimes referred to as monomer, implying that the self-assembly involves aggregation or polymerization of the monomer on the surface being coated to form the amphipathic coating. Regardless of mechanism, the resultant amphipathic coating is water insoluble, in contrast to its water solubility in the solution used to form the coating. The water insolubility of the coating suggests the formation of a larger molecule, whether by polymerization or other mechanism. The term "hydrophobin" is also used to describe the water insoluble coating obtained from the hydrophobin starting material (monomer).

U.S. 2003/0134042 A1 discloses the heating of the amphipathic coating in the presence of surfactant after application to the surface to increase the stability of the coating. As demonstrated on TEFLON® polytetrafluoroethylene sheet in Examples 2 and 4 of this patent application publication, the heat/surfactant-treated coating desorbed less hydrophobin in the washing solution than the untreated coating. While improved stability/durability of the coating is desirable, this becomes an extra step that must be performed and requires heating that would be either inconvenient or undesirable by the applicator of the coating. For example, the coating of contact lenses would preferably be done at room temperature (15–25° C.), without the use of surfactant. In addition, the presence of surfactant during heat treatment, presents the problem of coating being contaminated by residual surfactant.

BRIEF SUMMARY OF THE INVENTION

The present invention provides stable/durably amphipathic proteinaceous coatings that do not require heating/surfactant treatment, by forming the coating on nanoporous polymer. The nano-sized pores of the polymer interact with the coating to surprisingly increase its stability/durability. Thus, one embodiment of the present invention can be described as a composite structure comprising nanoporous polymer having a proteinaceous amphipathic coating thereon.

Another unexpected result embodied in the composite of the present invention is that the oxygen permeability of the nanoporous polymer is substantially unimpaired by the coating thereon.

BRIEF DESCRIPTION OF THE SEQUENCE LISTINGS

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the amino acid sequence of the mature TT1 hydrophobin.

SEQ ID NO:2 is the DNA sequence encoding mature TT1 hydrophobin of *Talaromyces thermophilus. thermophilus*

SEQ ID NO:3 is the amino acid sequence of the precursor TT1 hydrophobin.

SEQ ID NO:4 is the DNA sequence encoding the precursor TT1 hydrophobin of *Talaromyces thermophilus.*

DETAILED DESCRIPTION OF THE INVENTION

Nanoporous materials are disclosed in the paper entitled Nanoporous Materials, published by Cientifica, Ltd, October, 2003, as being a wide variety of materials, including polymers, that have holes less than 100 nm in size. Methods of making nanoporous materials are also disclosed. The nanoporous polymer used in the present invention preferably has an average nanopore (opening) size of less than 50 nm and more preferably no greater than 5 nm. The nanoporous polymer can be hydrophilic or hydrophobic, and the proteinaceous amphipathic coating will adhere to the surface of the polymer, with the outer surface of the coating modifying the water wettability of the polymer surface, making it more wettable in the case of the nanoporous polymer being hydrophobic, or making it less wettable in the case of the nanoporous polymer being hydrophilic. In either case, the nanopores of the polymer interact with the coating to increase its stability/durability.

The preferred method for obtaining nanopores is to have the polymer be amorphous as is generally indicated by the polymer being free of crystalline structure as indicated by the absence of melting point for the polymer. In greater detail, by "amorphous" is meant that the polymer is non-crystalline as indicated by the heat of fusion as determined from the endotherm detected in differential scanning calorimetry (DSC) for the as-polymerized polymer being no more than 3 J/g, preferably no more than 1 J/g. Generally no endotherm is seen in a second DSC heating even if a weak endotherm is detected in the first heating. The maximum of 3 J/g is considered to indicate an amorphous polymer when the "background noise" in the DSC trace of the endotherm is about the same 3 J/g so that a heat of crystallization (fusion) is hardly detectable for the polymer. The amorphous state of the polymer is characterized by a sufficiently open molecular structure, and an absence of crystals of polymer, that small molecules such as the inert gases can permeate through films formed from these polymers.

A. Y. Alentiev et al., "High transport parameters and free volume of perfluorodioxole copolymers", J. Membrane Science 126, published by Elsevier Science B. V., pp. 123–132 (1997) discloses the effect of the amorphous polymer state, namely that the polymer has free volume, this being the difference between the true density of the polymer vs. the actual lower density arising from the present of nanopores being present in the polymer. This article found that free volume of the perfluorodioxole copolymer was as high as that of poly(trimethylsilyl propyne) (PTMSP) and higher than for fluorine-containing norbornene polymer. The positron annihilation lifetime method is disclosed for determination of free volume and from that pore size (called free volume elements) in the polymer, and the article reports average pore sizes of less than 1 nm: 5.9–6.4 Å (0.59–0.64 nm) for the dioxole copolymer, 6.7 Å (0.67 nm) for PTMSP. The free volume is attributed to the disordered state of the amorphous polymer as formed. The openings (pores) in the polymer surface communicate through the thickness of the polymer, typically fabricated as a film, so that oxygen can pass through the film. Such small pore sizes will typically form a barrier to hydrocarbon gases. Polymers having crystallinity, as formed, while having a low level of free volume (14–18% for PTFE) as reported in the Alentiev article, are nevertheless comparatively oxygen impermeable, i.e. they are not nanoporous. Melt-flowable partially crystalline fluoropolymers also have lower free volumes as indicated by their comparative oxygen impermeability.

The nanoporous structure of the polymer used in the present invention is to be distinguished from the microporous polymers structures that are used in such applications as filtration, such structures being formed from polymers such as polyimide, polysulfone, cellulose acetate, polyaramid and porous polytetrafluoroethylene available as GORETEX® sheeting, wherein the pore sizes are measured in micrometers. One micrometer=1000 nanometers. Thus, the nanopores in the polymer used in the present invention are much smaller than the pores in microporous polymer substrates.

While microporous polymer structures have oxygen permeability, because of their rather large "holes" in the polymer, partially crystalline polymers which are not treated or modified in some way to provide the micropores are barriers to oxygen as indicated by an oxygen permeability of less than 425 centi-Barriers (one centi-Barrier=(cm$^3$×cm/cm Hg cm$^2$) ×10$^{-8}$)). Partially crystalline polymers, by virtue of the presence of crystallinity in the polymer are not nanoporous. One of the techniques such as disclosed in the Cientifica publication mentioned above would have to be imposed on the polymer to make it nanoporous.

The preferred amorphous nanoporous polymers used in the present invention are the amorphous perfluoropolymers. One group of amorphous perfluoropolymers useful in the present invention are copolymers of tetrafluoroethylene (TFE) with perfluoroolefins containing 3 to 8 carbon atoms, preferably hexafluoropropylene (HFP), as disclosed in U.S. Pat. Nos. 5,543,217 and 5,663,255, or with perfluoro(alkyl vinyl ether) wherein the alkyl group contains 1 or 2 carbon atoms, as disclosed in U.S. Pat. No. 5,919,878. In both patents, the amount of comonomer copolymerized with the TFE is sufficient to provide the amorphous state for the resultant fluoropolymer. According to both patents, the minimum amount of HFP or perfluoro(ethyl vinyl ether) (PEVE) required for incorporation into the copolymer to provide the amorphous state is about 20 mol %. Less can be used if other comonomer is present. In the case of TFE/PEVE copolymer, the amount of perfluoro(methyl vinyl ether) (PMVE) can exceed the amount of PEVE, provided that the PEVE constitutes at least 15 wt % of the combined weight of PEVE and PMVE in the fluoropolymer.

Another group of amorphous fluoropolymers are those containing a perfluorinated aliphatic ring structure such as perfluoro-2,2-dimethyl-1,3-dioxole (PDD). The fluoropolymer can be a homopolymer of PDD. In another embodiment, the fluoropolymer is a copolymer of PDD (the perfluorodioxole polymers of Alentiev et al.), including copolymers having a complementary amount of at least one monomer selected from the group consisting of tetrafluoroethylene, perfluoro(methyl vinyl ether), vinylidene fluoride and chlorotrifluoroethylene. A preferred fluoropolymer, because of its high gas permeability, is a copolymer of PDD and a complementary amount of tetrafluoroethylene, especially such a polymer containing about 65–99 mole % of PDD. The amorphous polymer preferably has a glass transition temperature of at least about 140° C., and more preferably at least about 180° C. Glass transition temperature (Tg) is known in the art and is the temperature at which the polymer changes from a brittle, vitreous or glassy state to a rubbery or plastic state. Examples of these copolymers are disclosed in U.S. Pat. Nos. 4,754,009 and 4,935,477. The polymer may also be an amorphous copolymer of PDD with a complementary amount of at least one other comonomer, said copolymer being selected from dipolymers with perfluoro(butenyl vinyl ether) and terpolymers with perfluoro(butenyl vinyl ether) and with a third comonomer, wherein the third comonomer can be a perhaloolefin in which halogen is at least one of fluorine or chlorine, or a perfluoro(alkyl vinyl ether); the amount of the third comonomer, when present, preferably being at most about 40 mole % of the total composition. T$_g$ of such fluoropolymers range from about 260° C. for dipolymers with tetrafluoroethylene having low amounts of tetrafluoroethylene comonomer down to less than 100° C. for the fluoropolymers containing at least 60 mole % of tetrafluoroethylene. Other dioxole containing polymers that can be used in the present invention are those disclosed in U.S. Pat. No. 5,883,177, such as copolymers of TFE with 4,5,difluoro-2,2-trifluoromethyl-1,3-dioxole.

Another group of amorphous fluoropolymers useful in the present invention are the polymers having a perfluorinated aliphatic ring structure formed in polymerization of perfluoro(allyl vinyl ether) or perfluoro(butenyl vinyl ether, such as CF$_2$=CF—O—(CF$_2$)$_n$—CF=CF$_2$, where n=1 or 2, to form polymers containing the ring structure:

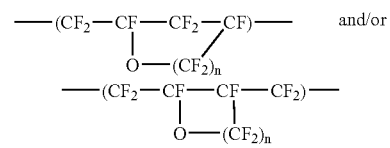

(where: n is an integer of 1 or 2); and copolymers thereof, as described in U.S. Pat. No. 4,897,457 of Nakamura et al.

The foregoing amorphous fluoropolymers are all nanoporous and thereby have oxygen permeability.

The starting material for the coating of the nanoporous polymer is the proteinaceous material which upon forming the coating exhibits its amphipathic nature. The proteinaceous material can have a wide range of amino acid sequences and can range in size from peptides to proteins. An example of protein are the hydrophobins, including hydrophobin-like material as described above. Hydrophobins are considered to be composed of about 70 to 125 amino acids, while modified hydrophobins may reach 150 amino-acids in length: typically the hydrophobin contains 8 cysteines in a conserved array. As disclosed in WO 2004/000880, the hydrophobin may be truncated into shorter amino-acid length, which are also useful in the present invention. Proteinaceous material having much longer lengths, such as greater than about 500 amino acids can also be used in the present invention. Examples of additional proteinaceous materials that can be used in the present invention are the hydrophobins and hydrophobin-like materials disclosed in U.S. 2003/0134042. Specific examples are the SC3 and SC4 hydrophobin (ca. 110 amino acids). These are class I hydrophobins. Examples of class II hydrophobins are HBI and HFBII (ca. 80 amino acids). Another example of hydrophobin is TT1 (ca. 135 amino acids), a class I hydrophobin from the thermophilic fungus *Taleromyces thermophilis*. This hydrophobin is described in greater detail below. Class I hydrophobins are insoluble in polar solvents such a ethanol and class II hydrophobins are soluble in these solvents Currently, over 50 hydrophobin sequences from a wide variety of fungal species are known, and are available, for example through GenBank and the national center for Biotechnology Information (NCBI, Bethsda, Md., and these hydrophobins are applicable to form the amphipathic coatings used in the present invention. The hydrophobin used in this coating process can contain other proteins, i.e., it need not be 100% pure.

The TT1 hydrophobin is a newly discovered thermophilic hydrophobin that is the subject of a U.S. patent application corresponding to docket identifier CL2504 filed on the same day as the present application. The amino acid and encoding DNA sequences for the mature TT1 protein, with secretion signal removed, are given as SEQ ID NOs:1 and 2, respectively. The amino acid and encoding DNA sequences for the precursor TT1 protein, with secretion signal intact, are given as SEQ ID NOs:3 and 4, respectively. "TT1 protein sample" refers to partially purified TT1 protein that is prepared from an expression system in which a polynucleotide encoding mature or precursor TT1 is expressed. In addition to TT1 protein, the sample may include other expression host proteins that are not excluded in the purification scheme. Preparation of a TT1 protein sample for the coating of the nanoporous polymers can be achieved through recombinant DNA technology. One skilled in the art will know how to prepare chimeric genes comprising the TT1 coding region that are suitable for expression of the precursor or mature TT1 protein in a production system. Preferred production systems are secretion systems which include, but are not limited to, bacterial expression systems such as *Bacillus* (Nagarajan, V et al. 1992 Gene 114:121–126), yeast expression systems such as *Saccharomyces* and *Pichia*, and fungal systems such as *Trichoderma* (Berquist, P. L. et al. 2004 32:293–7) and *Aspergillis* (Gouka, R. J. et al. 1997 Appl Mictobiol Biotechnol 47:1–11). For expression, the TT1 coding region is operably linked to a promoter that is functional in the desired host, and optionally to other regulatory signal sequences, to produce a chimeric gene. When using the DNA encoding the mature TT1 protein, to direct secretion it is necessary to include operably linked in the chimeric gene a polynucleotide sequence encoding a secretion signal peptide. The secretion signal peptide may be that derived from the precursor TT1 protein, or it may be derived from a heterologous gene. Examples of secretion signal peptides used in *Bacillus* expression systems are described in Nagarajan, V. et al. (1992, Gene 114:121–126). Secretion signal peptides for use in an expression system may be derived from a protein that is secreted in that host, for example, hydrophobin signal peptides may be used for secretion in fungal expression systems.

Various tags may be added to a chimeric gene that result in the expression of a peptide tag attached to the expressed protein. The use of these tags is known to those skilled in the art, for example, for detecting and purifying the expressed protein, since antibodies to the tag peptide or means of adsorbing the tag peptide to a substrate are available. Examples of such tags are the Flag tag and the His tag.

The chimeric gene construction for expression of TT1 in *Trichoderma* contains the following components, in the following order:

1) the promoter from the *Trichoderma* cbh1 (cellulase) gene
2) the polynucleotide encoding the secretion signal peptide of the cbh1 precursor protein
3) the polynucleotide encoding the mature TT1 protein with no translation stop codon
4) a polynucleotide encoding the Flag octapeptide and a His (6×) tag, incorporated to facilitate screening of fungal transformants and to aid in purification, followed by a translation stop codon
5) the transcription termination sequence from the cbh1 gene Plasmid vectors comprising the TT1 chimeric gene may be constructed for transfer of the chimeric gene into a host. The choice of plasmid vector is dependent upon the selected host and the method that will be used to transform the host cells. Expression vectors containing regulatory sequences that direct high level expression of foreign proteins, marker genes, and replication origins, if desired, are well known to those skilled in the art. The skilled artisan is well aware of the genetic elements that must be present on the plasmid vector in order to successfully transform, select and propagate host cells containing the recombinant DNA construct or chimeric gene. For example, a selection marker gene may be included, which is used to identify transformants. Transformation of the recombinant DNA vector may result in a plasmid being a transient or replicating stable resident of the host cell, or in integration of all or a segment of the introduced DNA into the host genome. Integration vectors generally include polynucleotides of homologous sequence to the host genome for targeted integration. The skilled artisan will also recognize that different independent integrative stable transformation events will result in different levels of expression and thus that multiple events must be screened in order to obtain lines displaying the desired expression level. Such screening may be accomplished by Southern analysis of DNA, Northern analysis of mRNA expression, Western analysis of protein expression, or phenotypic analysis.

TT1 is preferably produced in a fungal expression system using methods familiar to one skilled in the art as described for *Schizophyllum* in Scholtmeijer, M et al. (2002 Applied and Environmental Microbiology 68: 1367–1373), for *Aspergillis* in Gouka, R. J. et al. (1997 Appl Mictobiol Biotechnol 47:1–11), and for *Trichoderma* in WO2000058342. Transformants containing the chimeric gene construction described above, identified through selection, are grown on cellulose-containing medium to induce expression of the cbh1 gene promoter. Production of TT1 is assayed through immunodetection using an anti-Flag antibody to identify the highest expressing strain. An antibody to TT1 can be prepared to the TT1 polypeptide by methods known to those skilled in the art, which can then serve as an alternative probe for immunodetection of TT1 in transformants.

In a fungal expression host, expression of the endogenous hydrophobin(s) may be blocked so that the endogenous hydrophobin(s) do not co-purify with the production hydrophobin. Endogenous gene expression may be blocked by methods known to those of skill in the art, for example by deleting the encoding gene or a portion of the gene, inserting a blocking sequence into the encoding gene, disrupting the promoter of the encoding gene, expressing an antisense RNA to the endogenous hydrophobin messenger RNA and other such methods. It is preferred that in the *Trichoderma* expression host strain the endogenous HFB II hydrophobin expression is eliminated for production of TT1.

The expressed TT1 protein may be partially purified using hydrophobin protein purification methods known to those skilled in the art. These methods generally involve the formation of a foam that incorporates the hydrophobin on its surface. The foam may be created by methods such as releasing hydrogen bubbles from a Pt cathode positioned at the bottom of a container with the anode under the surface of the medium (Scholtmeijer et al., 2002, Appl and Envrt. Microbio. 68:1367–1373), and by rapid mixing. The foam sample is harvested and then lyophilized. The sample may be resuspended in trifluoroacetic-acid (TFA) which is then removed by evaporation to dryness, and the sample is resuspended in water. The TT1 foam sample may be dissolved directly in water, and desalted using 15 mM ammonium acetate at pH 7.5. An alternative hydrophobin purification method is to adsorb the hydrophobin to a surface, then to solubilize the adsorbed hydrophobin by incubating in a solution containing a surfactant at a temperature lower than 90° C., and to separate the resulting hydrophobin-enriched solution (US20030166960). The partially purified hydrophobin can be used in materials coating applications as described below. Alternatively, further purified TT1 protein may be prepared using the His tag, a TT1 antibody, or other protein purification methods known to those skilled in the art.

Prior to TT1 coating studies, lyophilized powder of TT1 protein sample may be suspended in a small volume of trifluoroacetic acid, evaporated to dryness and then resuspended and diluted in degassed water. The concentration of TT1 may be estimated by separating the proteins in the sample by gel electrophoresis, and visually inspecting the proteins stained with coomasie. An estimate of the % of TT1 protein in the sample of known protein concentration provides the protein concentration of TT1. Additional proteins that co-purify with TT1 may be included in the TT1 coating. A TT1 coating may be any amount of TT1 that is retained on a material surface such that the water contact angle of that surface is changed by about 15°, more preferably at least 20°.

The present invention finds that both classes of hydrophobins are stable and durable as coatings on nanoporous polymer. An example of a much longer length amphipathic proteinaceous material is bovine serum albumin (BSA), which is available from Sigma, and is made up of more than 500 amino acid units.

All of the proteinaceous starting materials are soluble in water so that a water solution can be used to apply the coating to the nanoporous polymer substrate. The application typically involves immersing the substrate in the solution for a period of time to obtain the coating desired. The immersion is preferably carried out at room temperature and may last for hours, although the TT1 hydrophobin exhibits the advantage of increased rate of coating formation when the coating operation is carried out at elevated temperatures. During the immersion the attraction of the nanoporous polymer substrate for its hydrophilic or hydrophobic domain of the proteinaceous material results in the formation of a coating on the substrate. This hydrophobin coating is insoluble in the solution from which the coating is derived. When the substrate is hydrophobic, the exposed surface of the coating tends towards hydrophilicity, i.e. exhibits a lower contact angle than the substrate prior to coating. When the substrate is hydrophilic, the exposed surface of the coating tends towards hydrophobicity, i.e. exhibits a higher contact angle than the substrate prior to coating. Typically, such coating is also insoluble to washing with warm (37° C.) tap water at a typical water-tap flow rate of 1 liter/min for 5 min. The coating is then air dried at room temperature.

The coating is so thin that it is not visible; thickness is generally no greater than about 10 nm, but its presence is established by measuring wetting angle on the surface of the coating and comparing this wetting angle with that of the polymer substrate. Preferably, the amphipathic coating produces at least about a 15° change in wetting angle, more preferably at least 20°. Wetting angle as described herein is measured by the sessile drop technique as described in van der Mei, H. C. et al. 1991, Microbial Cell Surface Analysis, pp. 261–267, edited by D. S. Mozes et al., VCH, New York, using a Krus DSA MK2 instrument and drop shape analysis software program. Perfluoropolymers typically exhibit a wetting angle of about 110°, which is lowered by a proteinaceous coating of the present invention to preferably at least to 90°, more preferably at least to 75°, and even more preferably at least to 60°. Some functional perfluoropolymers such as copolymer of TFE with about 15 mol % PSEPVE (perfluoro-3,6-dioxa4-methyl-7-octenesulfonyl fluoride) exhibit a contact angle of 90° and is still considered to be hydrophobic, and formation of a proteinaceous coating on a substrate of this polymer exhibits a contact angle of 70° and less. Conversely, hydrophilic polymers exhibiting a contact angle of less than 60° when coated according to the present invention, exhibit a contact angle of at 75°, and more preferably at least 90°.

While the coating thickness is very small, it functions to modify the water wettability of the polymer substrate, as will be shown in the Examples. The thickness of the coating however, with respect to the size of the nanopores in the polymer substrate, is rather massive, and indeed the coating method of immersion of the nanoporous polymer substrate in the coating solution provides the opportunity for the dissolved amphipathic proteinaceous material to enter into the pores. Some entry is evident by the increased stability/durability of the coating on nanoporous polymer. Surprisingly, the oxygen permeability of the coated nanoporous polymer substrate is nevertheless quite high, preferably at least about 80% of the permeability prior to forming the coating on the polymer substrate.

Amorphous fluoropolymers, because of their high oxygen permeability, especially in case of the PDD dioxole perfluoropolymer, would be especially useful as contact lenses. Such lenses would be more breathable (have higher oxygen transport) than any other available contact lens material, e.g.

at least 5× more permeable to oxygen than any other available lens material. Amorphous fluoropolymers, however, are hydrophobic, having a water contact angle of greater than about 95°. The composite structures of the present invention, in which the nanoporous polymer is in the form of an amorphous perfluoropolymer film, provide a water wettable surface arising from the proteinaceous amphipathic coating on the film, making such composite structure useful as a contact lens. Film is only one structure for the nanoporous polymer for coating in accordance with the present invention. Such film can be supported or unsupported and can be uniplanar, curved or formed into an annular shape such as tubing. In all these forms, the nanoporous polymer, even after coating, acts as a membrane, permitting passage of the desired molecular species, such as oxygen, therethrough. Other uses for the composite structure of the present invention include windows for underwater application such as optical sensors, water-wettable cladding for liquid core wave guides, water wettable degassing tubes or membranes, hydrophobicizing water-wettable surfaces such as carbonized PAN or PMMA sheeting for fuel cell diffusers, hydrophobicizing water-wettable fabrics for breathable, but non water-wettable outerwear, footwear, headgear, and sports equipment.

EXAMPLES

Methods

Preparation of proteinaceous material solutions: Purified hydrophobin HFBII as prepared by Bailey et al. 2002, Appl. Microbiol. Biotechnol 58 721–727 and Linder et al. 2001, Biomacromolecules 2, 511–517, was purchased from VTT Biotechnology (Finland). The hydrophobin SC3 was purified from culture filtrates of Schizophylum commune ATCC 44200 as described by Wosten et al 1993, Plant Cell. 5, 1567–1574, and Scholtmeijer et al 2002, Appl. Environ. Microbiol. 68, 1367–1373. Hydrophobin TT1 was obtained by cloning and overexpression in Trichoderma reesei by VTT Bioechnology (Finland). Lyophilized powder of TT1 fusion protein was dissolved in a small volume of trifluoroacetic acid which was evaporated to dryness and then redissolved and diluted in degassed water. Solutions of the other hydrophobins were prepared as follows. Lyophilized HFBII powder was resuspended directly into deionized and degassed water. Lyophilized SC3 powder was resuspended in a small volume of trifluoroacetic acid (TFA) which was evaporated to dryness with a stream of nitrogen and then resuspended in degassed water (WO 01/57528 A1). Bovine serum albumin BSA (ca 660 amino acids), obtained from Sigma (Aldrich lyophilized powder, catalog no. 7030) is made into solution by dissolving in degassed water. Protein conentrations of all hydrophobin lyophilized powders are determined using the Bicinchoninic Acid Protein Assay Kit supplied by Sigma (Sigma procedure No. TPRO-562). Appropriate dilutions are prepared to provide the hydrophobin concentrations in the examples below.

Surface Coating with proteinaceous material for amphipathic coatings on nanoporous polymer: Coating of an amorphous copolymer of tetrafluoroethylene/perfluoro-2,2-dimethyl-1,3-dioxole films, available as TEFLON® AF 2400 amorphous fluoropolymer, having an average pore size of about 0.6 nm is carried out on cleaned (acetone, ethanol and water washes) and dried polymer surface. The clean dry film has a WCA (water contact angle) of 110° C. Small film strips (0.8×22 mm) of the copolymer are immersed in the solutions of proteinaceous materials having the concentrations indicated in the Examples at room temperature for 16 hours. The immersed strips are removed from the solutions, rinsed with distilled water and air dried. The WCA is determined on the coated air-dried composite structure. Surface hydrophobicity or hydrophilicity is determined via WCA measurements using the sessile drop technique with a Krus DSA MK2 instrument and a drop shape analysis software program. It is inferred from change in WCA measurements from uncoated film surface as compared to coated film surface, that the amphipathic proteinaceous coating is present.

Robustness of amphipathic proteinaceous coatings: The robustness or stability of amphipathic proteinaceous coated surfaces is evaluated by washing the coating with full force (1 liter/min), warm (37° C.) tap water for 5 min, followed by drying the coated film at room temperature (for simplicity, this exposure is referred to as Tap Water) and retesting WCA of the coated film. More severe treatments are also used as will be described in Example 3.

Example 1

In this Example, the proteinaceous material is BSA in varying solution concentrations as shown in Table 1. The WCA of the coated film is determined after application of the coating from each solution and then again after the coating is exposed to Tap Water. These experiments are repeated on film samples, cleaned and dried in the same way as the films of TEFLON® AF2400, wherein the polymer film is commercially available partially crystalline copolymer of tetrafluoroethylene/-perfluoro(propyl vinyl ether) having a melting temperature of about 305° C.), available as TEFLON PFA 1000LP fluoropolymer (DuPont Company, Wilmington Del. USA) and having a WCA of 110°, with these results also being shown in Table 1.

TABLE 1

| BSA Coating of Teflon ® AF2400 and Teflon ® PFA 1000LP | | | | |
|---|---|---|---|---|
| | Water Contact Angle (degrees) | | | |
| BSA Conc. | Teflon ® AF2400 | | Teflon ® PFA 1000LP | |
| (μg/ml) | No Treatment | Tap Water | No Treatment | Tap Water |
| 100 | 101 | 99 | 99 | 106 |
| 500 | 80 | 73 | 80 | 95 |
| 1000 | 81 | 74 | 77 | 85 |
| 2500 | 59 | 55 | 63 | 87 |

As shown in Table 1, for both the AF and PFA polymers, the wettability increases (contact angle decreases) with increasing concentration of BSA in the coating solution. Exposure to Tap Water, however, rather than increasing WCA, which would indicate instability and lack of durability of the coating, shows further reduction in WCA. In contrast, the WCA of the coating on the PFA polymer increased with the exposure to Tap Water. Similar results are obtained with other amphipathic proteinaceous coatings. Thus, the nanoporous structure of the amorphous polymer substrate increases stability/durability of the coating as compared to the partially crystalline PFA polymer, which because of its partial crystallinity is not nanoporous.

Example 2

This Example shows in Table 2 the results of coating of nanoporous polymer with a variety of proteinaceous materials from aqueous solution, as described above, and the resultant reduction of WCA.

TABLE 2

Hydrophobin and Bovine Serum Albumin Coating of Teflon ® AF2400

| Protein | Immersion Protein Concentration (μg/ml) | Water Contact Angle (degrees) |
|---------|----------------------------------------|------------------------------|
| HFBII   | 220     | 54  |
| SC3     | 50      | 38  |
| BSA     | 2500    | 62  |
| BSA     | 1000    | 78  |
| None    | Control | 110 |

Example 3

This Example shows in Table 3 the robustness of the coating on nanoporous polymer, beyond exposure to Tap Water. Upon exposure to Tap Water, the SC3 and BSA coatings show little change in WCA, while the WCA of the HFBII increases to a level which was nevertheless considerably smaller than the WCA of the uncoated polymer. Exposure to the conditioning solution has a lesser effect than Tap Water on the HFBII coating. The BSA coating shows the least change in WCA upon this exposure. The next more stringent exposure treatment is the enzyme solution which is designed to remove protein from contact lenses. Performance of the HFBII coating is as good as when exposed to Tap Water. The SC3 coating also performs admirably, while the BSA coating shows little increase in WCA. The stability and durability of the proteinaceous coatings are such that they withstand removal by solution designed to remove protein. The exposure to Boston cleaner is the most stringent treatment, which removes most of not all of the proteinaceous coating as indicated by restoration of the WCA of the uncoated polymer. In this Example the contact with the cleaner, conditioning and enzyme solutions is according to the label instructions of the manufacturer (Boston).

TABLE 3

Hydrophobin and Bovine Serum Albumin Removal from Teflon ® AF2400

Water Contact Angle (degrees)

Surface Cleaning

| Protein (μg/ml) | Tap Water | | Boston Cleaner | | Boston Conditioning | | Boston Enzyme | |
|---|---|---|---|---|---|---|---|---|
|  | Initial | Final | Initial | Final | Initial | Final | Initial | Final |
| HFBII (220) | 54 | 70 | 56 | 109 | 56 | 63 | 54 | 70 |
| SC3 (50) | 36 | 35 | 36 | 107 | 38 | 48 | 38 | 44 |
| BSA (2500) | 64 | 68 | 59 | 110 | 63 | 59 | 59 | 69 |

The Boston Conditioning, Enzyme, and Cleaner solutions are described for contact lens application by the manufacturer as follows:

Boston Advance Comfort Conditioning Solution: a sterile aqueous, buffered slightly hypertonic solution containing a cationic cellulose derivative polymer, a cellulosic viscofier, polyvinyl alcohol and a derivatized polyethylene glycol as a wetting agent and cushioning agents; preserved with chlorhexidine gluconate (0.003%), polyaminopropyl biguanidine (0.0005%) and edetate disodium (0.05%) for destroying harmful organisms when used with Boston Advance Cleaner.

Boston Liquid Enzymatic Cleaner: a sterile aqueous solution containing proteolytic enzyme (subtilisin) as the active ingredient and glycerol. Preservative-free for removal of protein deposits.

Boston Advance Cleaner: a sterile, concentrated homogeneous surfactant solution containing alkyl sulfate, ethoxylated alkyl phenol, tri-quaternary cocoa-based phospholipid and silica gel as cleaning agents with titanium dioxide for cleaning fluoro silicone acrylate and silicone acrylate rigid gas permeable contact lenses.

Example 4

This Example shows the surprising retention of oxygen permeability of the coated nanoporous polymer. Oxygen permeability is determined according to the procedure in ASTM D 3985–95. The results are shown in Table 4. From these results, it is apparent that the oxygen permeability of the uncoated polymer is extremely high. While coatings of HFBII and TT1 (16 μg/lm concentration in solution) reduce wetting angle by at least 43%, at least 85% of the original oxygen permeability of the polymer is retained.

TABLE 4

Oxygen Permeation of Hydrophobin Coated Teflon ® AF2400

| Sample | Water Contact Angle (degrees) | $O_2$ Permeation [(mil*cc)/($m^2$*day)] |
|--------|-------------------------------|------------------------------------------|
| Control | 111 | 2,877,000 |
| HFBII   | 64  | 2,621,000 |
| SC3     | 30  | 2,532,000 |
| TT1     | 61  | 2,441,000 |

What is claimed is:

1. Composite structure comprising nanoporous amorphous fluoropolymer having a proteinaceous amphipathic coating thereon, said coating being applied without heat, wherein the pores of said polymer have an average diameter of no greater than about 5 nanometers and wherein said nanoporous polymer is hydrophobic, characterized by a wetting angle of at least about 90°.

2. The composite structure of claim 1 wherein said proteinaceous amphipathic coating increases the water wettability of said polymer, said increased water wettability being characterized by a reduction in wetting angle of at about least about 15°.

3. The composite structure of claim 1 having the oxygen permeability of at least about 80% of the oxygen permeability of said nanoporous polymer.

4. The composite structure of claim 1 wherein said nanoporous polymer is a film.

5. The composite structure of claim 4 wherein said film is a contact lens.

6. The composite structure of claim 1 wherein said proteinaceous amphipathic coating is hydrophobin.

* * * * *